United States Patent
Willis et al.

(10) Patent No.: US 7,915,186 B2
(45) Date of Patent: Mar. 29, 2011

(54) SKIN CONTACTING PRODUCT AND METHOD OF MAKING SAME

(75) Inventors: William H. Willis, Lake Forest, IL (US); James J. Passalaqua, Paddock Lake, WI (US)

(73) Assignee: Hollister Incorporated, Libertyville, IL (US)

( * ) Notice: Subject to any disclaimer, the term of this patent is extended or adjusted under 35 U.S.C. 154(b) by 311 days.

(21) Appl. No.: 11/717,569

(22) Filed: Mar. 13, 2007

(65) Prior Publication Data

US 2008/0226864 A1 Sep. 18, 2008

(51) Int. Cl.
*B32B 27/12* (2006.01)
*B32B 27/32* (2006.01)

(52) U.S. Cl. .................................. 442/394; 442/398

(58) Field of Classification Search .................. 442/394, 442/398
See application file for complete search history.

(56) References Cited

U.S. PATENT DOCUMENTS

| | | | |
|---|---|---|---|
| 5,455,091 A | 10/1995 | Oreglia et al. | |
| 5,897,541 A | 4/1999 | Uitenbroek et al. | |
| 6,015,605 A * | 1/2000 | Tsujiyama et al. | 428/195.1 |
| 6,106,507 A | 8/2000 | Botten et al. | |
| 6,887,222 B2 | 5/2005 | Mandzij et al. | |
| 2004/0147887 A1 | 7/2004 | Hagstroem et al. | |
| 2005/0084634 A1* | 4/2005 | Giori | 428/35.2 |
| 2005/0090788 A1 | 4/2005 | Shimada et al. | |
| 2005/0131360 A1 | 6/2005 | Villefrance et al. | |
| 2005/0273064 A1 | 12/2005 | Dircks et al. | |

FOREIGN PATENT DOCUMENTS

EP 1693193 8/2006

OTHER PUBLICATIONS

International Search Report for International Application No. PCT/US2008/050964, dated Jun. 13, 2008.
Written Opinion for International Application No. PCT/US2008/050964, dated Jun. 13, 2008.

* cited by examiner

*Primary Examiner* — Norca L Torres-Velazquez
(74) *Attorney, Agent, or Firm* — Marshall, Gerstein & Borun LLP

(57) ABSTRACT

The present disclosure is directed to a skin contacting product and a method of making same wherein the skin contacting product is formed of a laminated material having at least two distinct layers including a fabric layer and a film layer. The laminated material also has a film-like surface on a selected surface portion of the fabric layer which is formed by applying heat to the selected surface portion. The heat is applied at a temperature and for a period of time sufficient to form the film-like surface wherein the temperature and the period of time are dependent upon the physical characteristics of the laminated material.

25 Claims, 3 Drawing Sheets

SKIN CONTACTING PRODUCT AND METHOD OF MAKING SAME

FIELD OF THE DISCLOSURE

The present invention is generally directed to an improvement to enhance the usefulness of laminated materials, and more particularly, to a skin contacting product and method of making same that has a film-like surface on an area of a fabric-like material.

BACKGROUND OF THE DISCLOSURE

Skin contacting products such as body wearable collection devices are formed of material(s) having certain known desirable characteristics. If the collection device comprises a body waste collection pouch, these characteristics typically include the ability to receive and hold human body wastes of the type experienced in ostomy, continence and wound care for a determinable period of time while also typically serving as a satisfactory gas and odor barrier while being used. Further, it would be highly desirable to form such skin contacting products of a laminated material having a non-woven or other fibrous or fabric-like surface.

At the present time, there are commercially available films which are known to be particularly effective in many respects for these types of products. The films are known to be useful in devices which are generally capable of receiving and holding human body waste material and, if desired, the films can be formed so as to provide the requisite gas and odor barrier characteristics. However, the known commercially available films also are less than desirable in terms of certain other desirable characteristics.

In particular, films which are currently available are sometimes unacceptable as to "hand" or "feel". They have a tendency to stick against the body in hot or humid conditions and/or after showering, which is known to cause discomfort to the user of skin contacting products. Further, commercially available films have a tendency to produce an undesirable crinkling noise in use.

To counteract these problems, it has been proposed to laminate the film with a non-woven or other fibrous or fabric-like layer. This may be accomplished by thermally securing the surface of the film to such a layer. It has been suggested that this covering arrangement will achieve sound-deadening as well as a better "hand" or "feel".

However, skin contacting products such as body wearable collection devices usually require the ability to attach components thereto. And it is known to be difficult to attach components to what may be a "fuzzy" non-woven or fibrous or fabric-like exterior surface of body wearable collection devices. When components are adhesively attached to such a material, the anchorage is usually quite weak and there is the potential for leaks.

As will be appreciated, this is because the binding method only locks onto individual fibers of the fuzzy material which is commonly used to form the body wearable collection device. In the case of using an adhesive as an attachment method for attaching components to such a material, the adhesive does not wrap around every one of the fibers and, as a result, there is the potential for leak paths in the fuzzy material. For this reason, there has remained a need to develop a skin contacting product addressing all of the noted problems including the ability to attach components in a secure manner to the fuzzy material.

SUMMARY OF THE DISCLOSURE

Accordingly, the present disclosure is directed to a skin contacting product formed of a laminated material. The laminated material has at least two distinct layers including a fabric layer which is attached to a film layer. The laminated material also has a film-like surface which is formed on a selected surface portion of the fabric layer. The film-like surface is formed by applying heat to the selected surface portion on the fabric layer side of the laminated material.

In connection with the foregoing, the heat is applied at a temperature and for a period of time sufficient to form the film-like surface wherein the temperature and the period of time will be dependent upon the physical characteristics of the fabric layer used for the skin contacting product.

In an exemplary embodiment, the laminated material has three distinct layers including a fabric layer, a film layer and an adhesive layer therebetween which causes the fabric layer to be adhered to the film layer.

Preferably, the fabric layer of the material is comprised of a natural or synthetic fabric selected from one of cotton, silk, cellulosic tissue, nylon, polypropylene, polyester, polyethylene or other polyolefins or copolymers or blends thereof. It is also advantageous for the adhesive layer to be formed by applying a substantially continuous adhesive layer between the fabric layer and the film layer and activating or curing the adhesive to bond the fabric layer to the film layer. The film layer may be comprised of a monolithic film having both odor barrier properties and sealing properties whereby the laminated material is well suited for use as a skin contacting product such as a body wearable collection device.

Alternatively, the film layer may be comprised of a multi-layer film having at least an odor barrier sublayer and a sealing sublayer in which case the odor barrier sublayer may be comprised of polyethylene or other polyolefins or copolymers or blends thereof.

In the exemplary embodiment, the film-like surface is advantageously formed by:
i) performing the step of applying heat to the selected surface portion of the material at a temperature of approximately 325° F. to 425° F. for a time of approximately 0.75 seconds to 1.75 seconds, and ii) performing the step of cooling the selected surface portion of the material at a temperature of approximately 60° F. to 100° F. for a time of approximately 1.0 second to 4.0 seconds after the heat applying step.

The present disclosure is also directed to a method of forming a film-like surface on a laminated material used for skin contacting products. The method includes the step of forming the material of at least two distinct layers. The two distinct layers include a fabric layer which is attached to a film layer. The method also includes the step of forming the film-like surface by applying heat. The heat is applied to a selected surface portion on the fabric layer side of the laminated material. The method also includes applying the heat at a temperature and for a period of time sufficient to form the film-like surface on the selected surface portion of the fabric layer.

Other objects, advantages and features of the present disclosure will be understood and appreciated from a consideration of the following specification taken in conjunction with the accompanying drawings.

DETAILED DESCRIPTION OF THE DISCLOSURE

Figure 1:
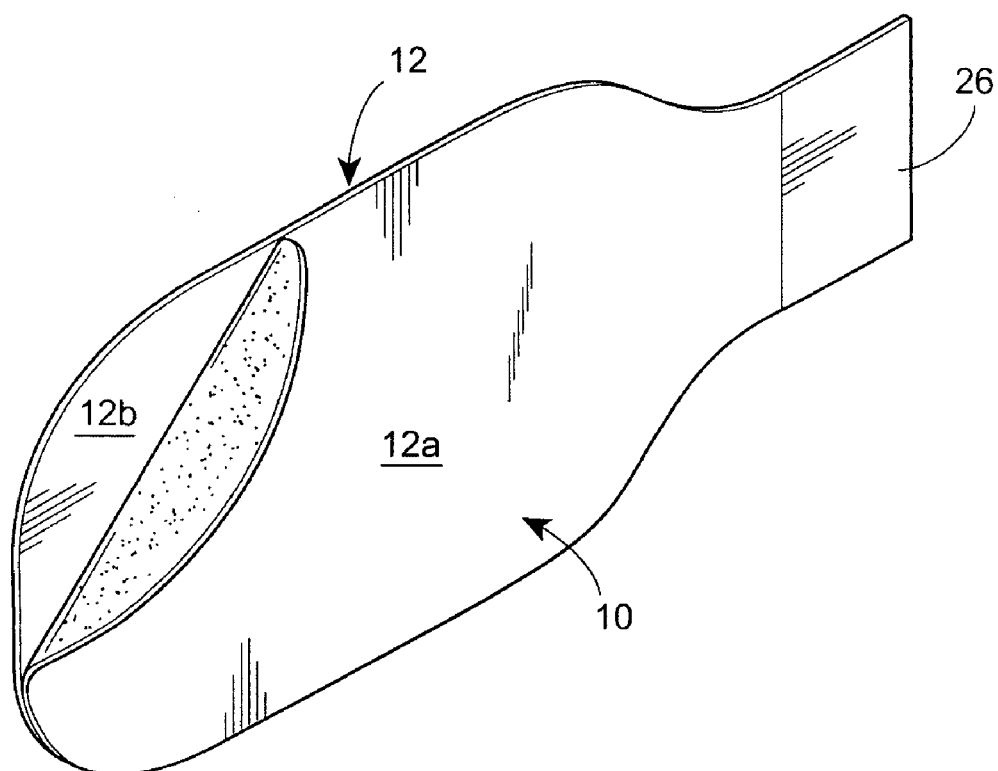
FIG. 1 is a prospective view of a skin contacting product formed of a laminated material and having a film-like surface on a selected surface potion according to the present disclosure.
Figure 2:
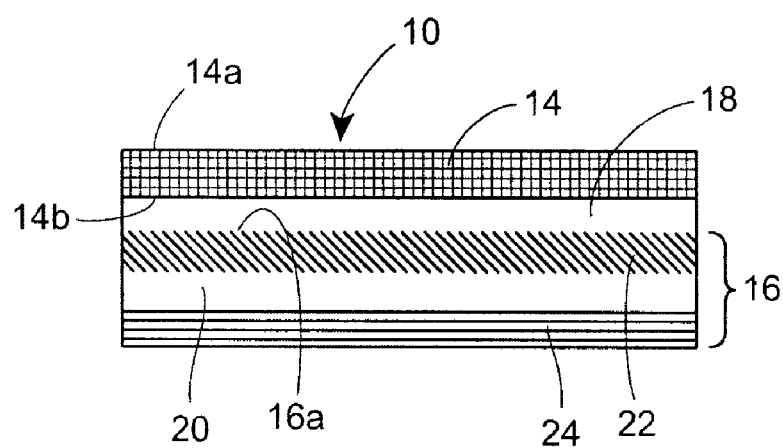
FIG. 2 is a cross-sectional view of the laminated materiel used to form the skin contacting product illustrated in FIG. 1.

In the illustrations given, and first with reference to FIGS. 1 and 2, the reference numeral 10 designates generally a laminated material which has been formed into a skin contacting product such as an ostomy pouch 12. The pouch 12 includes a pair of sidewalls 12a and 12b, and the laminated material 10 of each of the side walls 12a and 12b comprises at least two, and preferably three, distinct layers, i.e., a fabric layer 14 and a film layer generally designated 16, and preferably also an adhesive layer 18 disposed between the fabric layer 14 and the film layer 16 (see FIG. 2). With this arrangement, the adhesive layer 18 may comprise an adhesive provided in such a manner as, preferably, to substantially continuously bond the fabric layer 14 to the film layer 16.

Alternatively, the fabric layer 14 and the film layer 16 can form the laminated material 10 in any other suitable manner, e.g., thermal bonding through heat lamination.

Preferably, the fabric layer 14 is comprised of a natural or synthetic fabric selected from one of cotton, silk, cellulosic tissue, nylon, polypropylene, polyester, polyethylene or other polyolefins or copolymers or blends thereof. The adhesive layer 18 is formed by applying a substantially continuous layer of an adhesive between the fabric layer 14 and the film layer 16 and by then activating or curing the adhesive to bond the fabric layer to the film layer substantially as shown in FIG. 2. The film layer 16 may be comprised of a monolithic film characterized by having both odor barrier properties and sealing properties or, alternatively, it may be comprised of a multilayer film generally as illustrated in FIG. 2.

When the film layer 16 comprises a multilayer film, it preferably has at least an odor barrier sublayer 20 and a sealing sublayer 22 wherein the odor barrier sublayer 20 is comprised of polyethylene or other polyolefins or copolymers or blends thereof.

The film layer 16 can be formed as a multilayer film having up to about eight layers which makes it possible to provide multiple odor barrier layers such as 20. In addition, the film layer 16 can be formed as a multilayer film having a sealing sublayer on one side 22 or both sides 22 and 24. As also shown in FIG. 2, the sealing sublayer 22 forms an outer sealing sublayer 16a of the film layer 16, i.e., facing in the direction of the fabric layer 14.

The fabric layer 14 may also be laminated to the film layer 16 in such a manner that a brushed, sueded, or sheared side thereof comprises the outwardly facing side 14a of the fabric layer. This outwardly facing side 14a may face toward the skin of the user, in which case it may be thought of as a comfort panel, and/or it may face the user's clothing; in either case, treating the fabric layer 14 so it is brushed, sueded, or sheared is optional. Further, it is possible for the fabric layer 14 to be laminated to the film layer 16 in such a manner that the brushed, sueded, or sheared side comprises the inwardly facing side 14b of the fabric layer.

Regardless of these or other possible aspects of the fabric layer 14, it will be appreciated that the film-like surface is advantageously formed on the outwardly facing surface of the fabric layer in the manner disclosed herein because it is the outwardly facing surface to which ancillary components will be attached as described above and as further described below.

These features of the laminated material 10 as well as still additional features are disclosed in commonly owned and co-pending U.S. patent application of Dircks et al. for Laminated Material and Body Wearable Pouch Formed Therefrom, Ser. No. 10/861,560, filed Jun. 4, 2004, the teachings of which are hereby incorporated by reference.

Referring to FIG. 1, the skin contacting product shown is an ostomy pouch 12 having a film-like surface as at 26 on a selected surface portion of the material 10 on the side defined by the fabric layer 14. The film-like surface as at 26 is formed by applying heat to the selected surface portion of the laminated material 10. Specifically, the heat is applied to the selected surface portion at a temperature and for a period of time sufficient to form the film-like surface as at 26 which is dependent upon the physical characteristics of the material.

Using the disclosed materials, the film-like surface 26 is formed by applying heat to the selected surface portion at a temperature of approximately 325° F. to 425° F. for a time of approximately 0.75 seconds to 1.75 seconds. Further, the film-like surface is formed by thereafter cooling the selected surface portion at a temperature of approximately 60° F. to 100° F. for a time of approximately 1.0 seconds to 4.0 seconds after applying heat.

As will be appreciated, the film-like surface portion as at 26 is preferably formed on the side of the laminated material 10 defined by the fabric layer 14 and, more particularly, on the outwardly facing side 14a of the fabric layer 14 which may optionally be treated by brushing, sueding, or shearing to increase comfort on the skin of a user.

Figure 3:
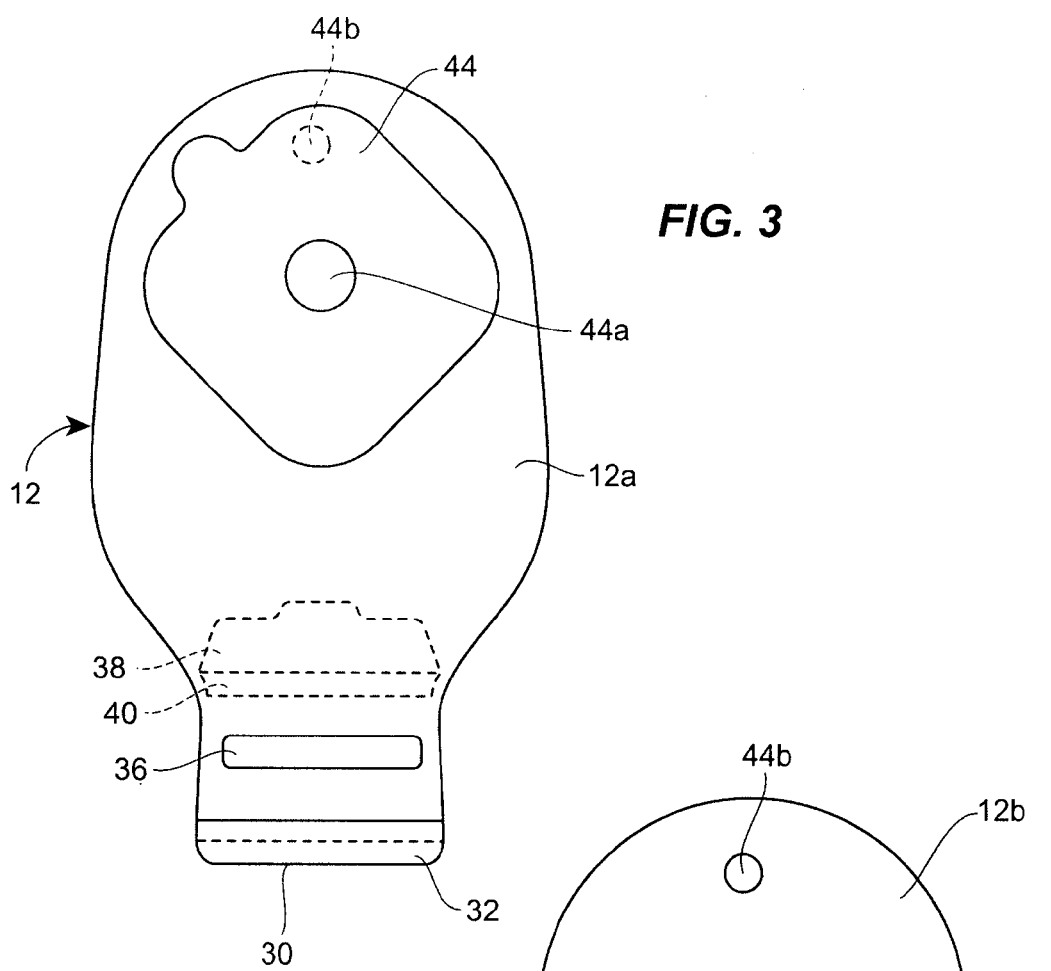
FIG. 3 is a schematic plan view of the skin contacting side of an ostomy pouch formed of the laminated material of FIG. 2.
Figure 4:
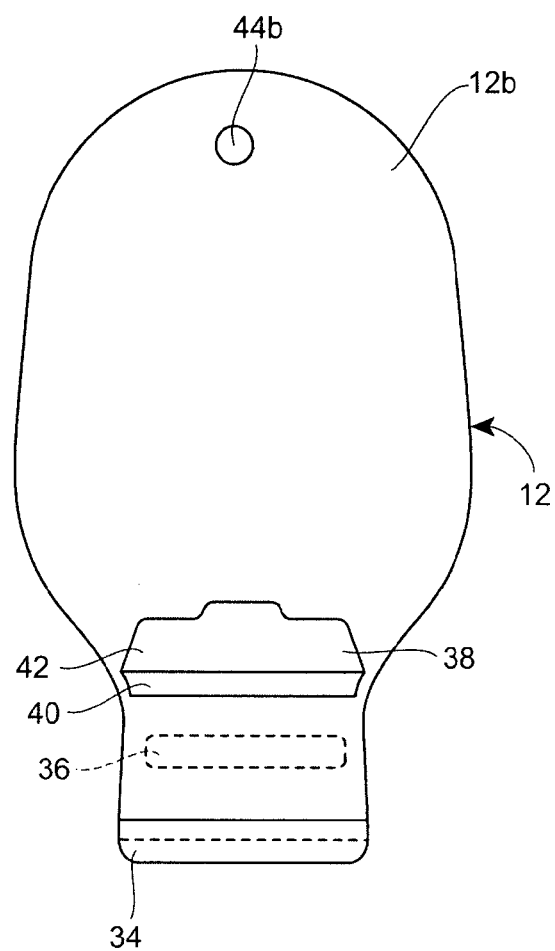
FIG. 4 is a schematic plan view of the opposite side of the ostomy pouch formed of the laminated material of FIG. 2.

In FIGS. 3 and 4, the skin contacting product is in the form of a fully assembled drainable ostomy pouch 12 having sidewalls 12a and 12b of flexible sheet material 10 defining a cavity therebetween and defining a downwardly-extending neck portion 28 terminating in a discharge opening 30 (see FIG. 1). The fully assembled ostomy pouch 12 includes stiffening strips 32 and 34 and a strip 36 of an interlocking means such as Velcro (hook or loop portion) or DUOTEC from G. Binder GmbH & Co., Germany (interlocking mushroom elements). The ostomy pouch 12 also includes a flap 38 of flexible film material which has an attachment edge portion 40 and a strip 42 of a corresponding interlocking means such as Velcro (loop or hook portion) or DUOTEC whereby the neck portion 28 can be folded upwardly for interlocking engagement of the respective strips 36 and 42.

Referring specifically to FIG. 3, the fully assembled ostomy pouch 12 may additionally include a face plate 44 having a stoma-receiving aperture 44a and an opening 44b for flatus gases.

In connection with ancillary components such as the stiffening strips 32 and 34, the interlocking engagement strips 36 and 42, and the face plate 44, it is important to be able to attach these components to a fuzzy non-woven or fibrous or fabric-like material of the type used for skin contacting products in a secure manner without interfering with performance. The normal result in the past has been a weak adhesive anchorage with the potential for leaks. However, by forming a film-like surface on selected surface portions of the fuzzy material in the areas where the ancillary components are to be attached, it is possible to utilize a non-woven or fibrous or fabric-like material for its desirable skin contacting properties while having robust adhesive bonding of the ancillary components to the film-like surface.

As will be seen by comparing FIG. 1 with FIGS. 3 and 4, substantially the entirety of the downwardly-extending neck portion 28 may have the film-like surface 26 formed thereon to facilitate the attachment of the ancillary components 32, 34, 36, and 38 in the appropriate locations so the neck portion can be folded up for interlocking engagement of the strips 36 and 38 and a similar film-like surface can be formed on one of the sidewalls 12a in the appropriate location to facilitate the attachment of the faceplate 44 by using a suitable conventional adhesive.

While the unique features of the disclosure have been discussed relative to an ostomy pouch having particular ancillary components attached thereto, it will be appreciated that the disclosed features are not limited in any way to either ostomy pouches or particular ancillary components but, rather, they are merely exemplary of the significant advantages which are to be derived from, and are inherent in, the present disclosure.

In another respect, the present disclosure is directed to a method of forming a film-like surface on a laminated material used for skin contacting products. The method includes the step of forming the material of at least two distinct layers. The two distinct layers include a fabric layer which is attached to a film layer. The method also includes the step of forming the film-like surface by applying heat. The heat is applied to a selected surface portion on the fabric layer side thereof. The method also includes applying the heat at a temperature and for a period of time sufficient to form the film-like surface on the selected surface portion.

In connection with the foregoing, the temperature and the period of time will be dependent upon the physical characteristics of the fabric layer used for the skin contacting product and, in an exemplary method, the laminated material has three distinct layers including a fabric layer, a film layer and an adhesive layer therebetween which causes the fabric layer to be adhered to the film layer.

As previously described, the fabric layer of the material is comprised of a natural or synthetic fabric selected from one of cotton, silk, cellulosic tissue, nylon, polypropylene, polyester, polyethylene or other polyolefins or copolymers or blends thereof. Furthermore, and as previously described, the adhesive layer is formed by applying a substantially continuous layer of an adhesive between the fabric layer and the film layer and by thereafter activating or curing the adhesive to thereby cause the fabric layer to become securely bonded to the film layer. Also as previously described, the film layer is comprised of a monolithic film characterized by having both odor barrier properties and sealing properties or, alternatively, of a multilayer film having an odor barrier sublayer and a sealing sublayer.

In practicing the method of the disclosure, if the film layer is a multilayer film, the odor barrier sublayer is comprised of polyethylene or other polyolefins or copolymers or blends thereof.

In other respects concerning the materials disclosed herein, the step of applying heat to the selected surface portion of the material is performed at a temperature of approximately 325° F. to 425° F. for a time of approximately 0.75 seconds to 1.75 seconds, and the method preferably includes the further step of thereafter cooling the selected surface portion of the material at a temperature of approximately 60° F. to 100° F. for a time of approximately 1.0 second to 4.0 seconds following the heat applying step.

Figure 5:
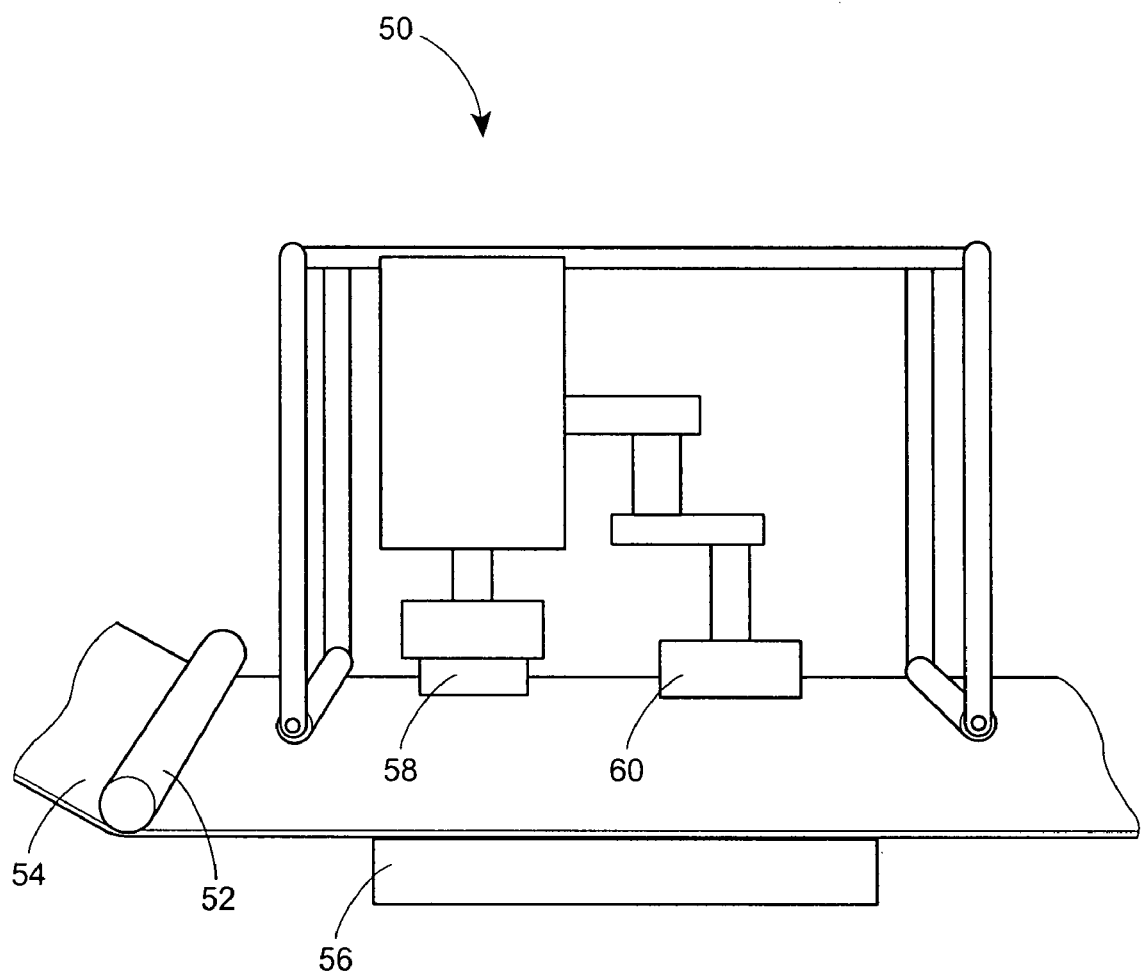
FIG. 5 is a schematic view of a device for performing a method of forming a film-like surface on a selected surface portion of a skin contacting product according to the present disclosure.

Referring to FIG. 5, the reference numeral 50 designates generally a device shown schematically for practicing the method of forming a film-like surface on a selected surface portion of a skin contacting product. The device 50 includes a roller 52 which directs a continuous belt 54 of the laminated material over a table 56. The device 50 also includes a heating press 58 and a cooling press 60 performing the heating and cooling steps on the laminated material 10 to form a film-like surface on a selected surface portion thereof.

As will be appreciated, the size, shape and location of the film-like surface can be controlled by controlling the location of the heating press 58 relative to the continuous belt 54, controlling the travel distance of the continuous belt 54 between each application of the heating press 58, and controlling the size and shape of the plate on the heating press 58, all of which are well within the ability of one skilled in the art.

While in the foregoing there has been set forth a detailed description of the present disclosure relative to a presently preferred embodiment, it will be appreciated that the details herein given may be varied by those skilled in the art without departing from the true spirit and scope of the appended claims.

What is claimed is:

1. A skin contacting product formed of a laminated material having odor barrier and sealing properties, wherein the material comprises:
    at least two distinct layers including a fabric layer bonded to a film layer, the fabric layer being comprised of a natural or synthetic fabric and the film layer being comprised of a film having the odor barrier and sealing properties, the fabric layer having an outwardly facing side comprising a fuzzy surface; and
    a film-like surface formed on a selected portion of the outwardly facing side of the fabric layer by applying heat to the fuzzy surface, the heat being applied at a temperature and for a period of time sufficient to change the fuzzy surface into the film-like surface on the selected portion of the outwardly facing side of the fabric layer, the film-like surface facilitating the attachment of an ancillary component to the selected portion of the outwardly facing side of the fabric layer.

2. The skin contacting product of claim 1 wherein the laminated material is formed of three distinct layers including an adhesive layer between the fabric layer and the film layer.

3. The skin contacting product of claim 1 wherein the natural or synthetic fabric comprising the fabric layer is selected from one of cotton, silk, cellulosic tissue, nylon, polypropylene, polyester, polyethylene or other polyolefins or copolymers or blends thereof.

4. The skin contacting product of claim 2 wherein the adhesive layer is formed by applying a substantially continuous layer of an adhesive between the fabric layer and the film layer and by activating or curing the adhesive to thereby bond the fabric layer to the film layer.

5. The skin contacting product of claim 1 wherein the film layer is comprised of a monolithic film having the odor barrier and sealing properties.

6. The skin contacting product of claim 1 wherein the film layer is comprised of a multilayer film having at least an odor barrier sublayer and a sealing sublayer to provide the odor barrier and sealing properties.

7. The skin contacting product of claim 6 wherein the odor barrier sublayer is comprised of polyethylene or other polyolefins or copolymers or blends thereof.

8. The skin contacting product of claim 1 wherein the film-like surface is formed by performing the step of applying heat to the fuzzy surface on the selected portion of the outwardly facing side of the fabric layer at a temperature of approximately 325° F. to 425° F. for a time of approximately 0.75 seconds to 1.75 seconds.

9. The skin contacting product of claim 8 wherein the film-like surface is formed by performing the step of cooling the selected portion of the fabric layer at a temperature of approximately 60° F. to 100° F. for a time of approximately 1.0 seconds to 4.0 seconds after the heat applying step.

10. A skin contacting product formed of a laminated material having odor barrier and sealing properties, wherein the material comprises:

at least two distinct layers including a fabric layer bonded to a film layer, the fabric layer being comprised of a natural or synthetic fabric and the film layer being comprised of a film having the odor barrier and sealing properties, the outwardly facing side of the fabric layer comprising a fuzzy surface; and a film-like surface formed on a selected portion of the outwardly facing side of the fabric layer by: i) applying heat at a temperature of approximately 325 to 425° F. for a time of approximately 1.0 to 4.0 seconds to change the fuzzy surface into the film-like surface on the selected portion of the outwardly facing side of the fabric layer, and ii) thereafter cooling the selected portion of the outwardly facing side of the fabric layer, the film-like surface facilitating the attachment of an ancillary component to the selected portion of the outwardly facing side of the fabric layer.

11. The skin contacting product of claim 10 wherein the laminated material is formed of three distinct layers including an adhesive layer between the fabric layer and the film layer.

12. The skin contacting product of claim 10 wherein the natural or synthetic fabric comprising the fabric layer is selected from one of cotton, silk, cellulosic tissue, nylon, polypropylene, polyester, polyethylene or other polyolefins or copolymers or blends thereof.

13. The skin contacting product of claim 11 wherein the adhesive layer is formed by applying a substantially continuous layer of an adhesive between the fabric layer and the film layer and by activating or curing the adhesive to thereby bond the fabric layer to the film layer.

14. The skin contacting product of claim 10 wherein the film layer is comprised of a monolithic film having the odor barrier and sealing properties.

15. The skin contacting product of claim 10 wherein the film layer is comprised of a multilayer film having at least an odor barrier sublayer and a sealing sublayer to provide the odor barrier and sealing properties.

16. The skin contacting product of claim 15 wherein the odor barrier sublayer is comprised of polyethylene or other polyolefins or copolymers or blends thereof.

17. In a drainable ostomy pouch having sidewalls of flexible sheet material having odor barrier and sealing properties, the sidewalls defining a cavity therebetween and a downwardly-extending neck terminating in a discharge opening, the improvement comprising: the flexible sheet material comprising a laminated material having at least two distinct layers including a fabric layer comprised of a natural or synthetic fabric bonded to a film layer comprised of a film having the odor barrier and sealing properties, the fabric layer having an outwardly-facing side comprising a fuzzy surface, and a film-like surface formed on the outwardly-facing side of the fabric layer on the downwardly-extending neck, the film-like surface being formed by: i) applying heat to the fuzzy surface of the fabric layer on the downwardly-extending neck at a temperature and for a period of time sufficient to change the fuzzy surface into the film-like surface, and ii) thereafter cooling the film-like surface on the downwardly-extending neck, the film-like surface facilitating the attachment of an ancillary component to the downwardly-extending neck on the outwardly facing side of the fabric layer.

18. The drainable ostomy pouch of claim 17 wherein the flexible sheet material is formed of three distinct layers including an adhesive layer between the fabric layer and the film layer.

19. The drainable ostomy pouch of claim 17 wherein the natural or synthetic fabric comprising the fabric layer is selected from one of cotton, silk, cellulosic tissue, nylon, polypropylene, polyester, polyethylene or other polyolefins or copolymers or blends thereof.

20. The drainable ostomy pouch of claim 18 wherein the adhesive layer is formed by applying a substantially continuous layer of an adhesive between the fabric layer and the film layer and by activating or curing the adhesive to thereby bond the fabric layer to the film layer.

21. The drainable ostomy pouch of claim 17 wherein the film layer is comprised of a monolithic film having the odor barrier and sealing properties.

22. The drainable ostomy pouch of claim 17 wherein the film layer is comprised of a multilayer film having at least an odor barrier sublayer and a sealing sublayer to provide the odor barrier and sealing properties.

23. The drainable ostomy pouch of claim 22 wherein the odor barrier sublayer is comprised of polyethylene or other polyolefins or copolymers or blends thereof.

24. The drainable ostomy pouch of claim 17 wherein the film-like surface is formed by performing the step of applying heat to the fuzzy surface of the fabric layer on the downwardly-extending neck at a temperature of approximately 325° F. to 425° F. for a time of approximately 0.75 seconds to 1.75 seconds.

25. The drainable ostomy pouch of claim 24 wherein the film-like surface is formed by performing the step of cooling the film-like surface on the downwardly-extending neck at a temperature of approximately 60° F. to 100° F. for a time of approximately 1.0 seconds to 4.0 seconds after the heat applying step.

* * * * *